United States Patent
Schleith et al.

(10) Patent No.: US 10,067,081 B2
(45) Date of Patent: Sep. 4, 2018

(54) APPARATUS FOR DETERMINING AND/OR MONITORING A LIMIT VALUE OF A PROCESS VARIABLE

(71) Applicant: Endress + Hauser GmbH + Co. KG, Maulburg (DE)

(72) Inventors: Christoph Schleith, Schopfheim (DE); Michael Dotsch, Rickenbach (DE)

(73) Assignee: ENDRESS + HAUSER GMBH + CO. KG, Maulburg (DE)

( * ) Notice: Subject to any disclaimer, the term of this patent is extended or adjusted under 35 U.S.C. 154(b) by 283 days.

(21) Appl. No.: 14/368,618

(22) PCT Filed: Nov. 22, 2012

(86) PCT No.: PCT/EP2012/073373
§ 371 (c)(1),
(2) Date: Jun. 25, 2014

(87) PCT Pub. No.: WO2013/097989
PCT Pub. Date: Jul. 4, 2013

(65) Prior Publication Data
US 2015/0107356 A1    Apr. 23, 2015

(30) Foreign Application Priority Data
Dec. 27, 2011  (DE) .......... 10 2011 089 941

(51) Int. Cl.
*G01N 11/00*  (2006.01)
*G01N 27/22*  (2006.01)
(Continued)

(52) U.S. Cl.
CPC ....... *G01N 27/228* (2013.01); *G01F 23/0069* (2013.01); *G01F 23/2967* (2013.01);
(Continued)

(58) Field of Classification Search
CPC .................................................. G01N 27/228
USPC ........................................................ 73/32 R
See application file for complete search history.

(56) References Cited

U.S. PATENT DOCUMENTS

| 4,412,450 A | 11/1983 | Franz |
| 5,672,975 A | 9/1997 | Kielb |

(Continued)

FOREIGN PATENT DOCUMENTS

| CN | 1187242 A | 7/1998 |
| CN | 1516808 A | 7/2004 |

(Continued)

OTHER PUBLICATIONS

PKP Prozessmesstechnik GmbH, Fullstandsmessung und -uberwachung FCS01, veroffentlicht 2004, archiviert Oct. 13, 2006, archive.org [online]. (Translation: Level Measurement and Monitoring FCS01, published 2004, Germany.

(Continued)

*Primary Examiner* — Walter L Lindsay, Jr.
*Assistant Examiner* — Philip Marcus T Fadul
(74) *Attorney, Agent, or Firm* — Bacon & Thomas, PLLC

(57) ABSTRACT

Apparatus for determining and/or monitoring at least one limit value of a process variable of a medium in a container, comprising at least one sensor unit for registering a measured value dependent on the process variable and at least one electronics unit for producing a measurement signal dependent on the process variable. The invention is distinguished by features including that the apparatus is embodied to draw energy via a voltage output and a digital input of a recorder apparatus or a process control system.

8 Claims, 2 Drawing Sheets

(51) Int. Cl.
  *G01F 23/00* (2006.01)
  *G01F 23/296* (2006.01)
  *G01N 9/00* (2006.01)
(52) U.S. Cl.
  CPC .............. *G01N 9/00* (2013.01); *G01N 11/00* (2013.01); *G01N 2011/0066* (2013.01)

(56) References Cited

U.S. PATENT DOCUMENTS

| | | | |
|---|---|---|---|
| 6,140,940 A | 10/2000 | Klofer | |
| 6,734,793 B1 | 5/2004 | Dreyer | |
| 7,634,939 B2 | 12/2009 | Drahm | |
| 8,380,142 B2 | 2/2013 | Ferreira | |
| 8,525,560 B2 | 9/2013 | Lalla | |
| 2003/0139146 A1 | 7/2003 | Mercier | |
| 2008/0127719 A1 | 6/2008 | Drahm | |
| 2012/0118043 A1* | 5/2012 | Heckler | H01H 33/563 73/30.02 |

FOREIGN PATENT DOCUMENTS

| | | |
|---|---|---|
| DE | 29917651 U1 | 12/2000 |
| EP | 0883097 A2 | 12/1998 |
| EP | 1134562 A1 | 9/2001 |
| EP | 2045791 A1 | 4/2009 |
| GB | 2081452 A | 2/1982 |
| WO | 9641135 A1 | 12/1996 |
| WO | 0245045 A1 | 6/2002 |
| WO | 2011131399 A1 | 10/2011 |

OTHER PUBLICATIONS

International Search Report, EPO, The Netherlands, dated Apr. 2, 2013.
German Search Report, DPMA, Munich, dated Aug. 1, 2012.
English translation of IPR, WIPO, Geneva, dated Jul. 10, 2014.
SO Zahler an einer SPS, internet discussion, 2011.
SPS-Formum-de, internet discussion, 2011.

* cited by examiner

APPARATUS FOR DETERMINING AND/OR MONITORING A LIMIT VALUE OF A PROCESS VARIABLE

TECHNICAL FIELD

The present invention relates to an apparatus for determining and/or monitoring at least one limit value of a process variable of a medium in a container, comprising at least one sensor unit for registering a measured value dependent on the process variable and at least one electronics unit for producing a measurement signal dependent on the process variable. The process variable is preferably the limit-level, the density, or the viscosity of a medium.

BACKGROUND DISCUSSION

Known from the state of the art are vibronic limit level switches, which monitor the limit-level of a liquid or a bulk good with the assistance of a mechanically oscillatable unit. The mechanically oscillatable unit, which is, for example, a rod in the case of bulk goods and a fork with two tines in the case of liquids, is excited such that it executes resonant oscillations. The oscillation excitement occurs, in such case, as a rule, by means of a piezoelectric or inductive transducer. If the degree of coverage of the oscillatable unit with the medium changes, whose limit-level is to be monitored, this influences the oscillation frequency of the oscillatable unit. By establishing a limit value and comparing the current oscillation frequency with the limit value, it can be detected whether the fill level of the medium exceeds or subceeds the limit-level. Modern vibronic limit level switches are able to determine the limit-level reliably even in the case of strongly accretion forming or foaming media. Such limit level switches are produced and sold by the applicant under the mark Liquiphant in a large number of variants.

Further known are limit level switches having at least one electrode and utilizing the capacitive or conductive principle. Another electrode or the container functions as counter electrode. The limit-level is measured capacitively via the capacitance of the capacitor formed of electrode and counter electrode varied by the medium acting as dielectric. In the case of conductive measuring, the conductive medium short circuits the electrode and the counter electrode.

The above-described limit level switches require electrical energy for measuring. The energy supply occurs, as a rule, via a 2-conductor connection with a voltage source. Via a third line, the limit level switch forwards the switch signal to a recording apparatus or to a control unit, for example, a programmable logic controller (PLC), for control of downstream field devices.

Making do without auxiliary energy and thereby with only two conductors are so called mechanical float switches. These are formed of a rod, which is introduced vertically into the measured liquid, and one or more magnetic floating bodies, which are freely movable in the vertical direction but guided by the rod. If the float reaches the fill level to be monitored, it closes an electrical contact and thereby connects an output and an input of a processing unit. Such mechanical float switches operate without auxiliary energy but are more wear susceptible than, for example, vibronic or capacitive, limit level switches.

SUMMARY OF THE INVENTION

An object of the invention is to provide an electronic apparatus for registering a limit value of a process variable and requiring only two connecting conductors.

The object is achieved by features including that that the apparatus is embodied to draw energy via a voltage output and a digital input of a recorder apparatus or a process control system.

The object is achieved by features including that the apparatus is embodied to draw energy via a voltage output and a digital input of a recorder apparatus or a process control system.

In a first embodiment, the measurement signal is a switch signal, which assumes one of two possible states as a function of the process variable.

In an embodiment, the apparatus includes a voltage control system, which connects the voltage output with the digital input.

In an embodiment, the voltage control system controls the terminal voltage of the apparatus as a function of the measurement signal.

In a further development, the voltage control system supplies the electronics unit with a constant power.

In a further development, the voltage control system has a changeable internal resistance.

In an embodiment, the downstream control apparatus and/or recorder apparatus is a programmable logic controller or a digital screen recorder.

In an embodiment, the process variable is a limit-level of a liquid or a bulk good in the container or a limit value for the density or the viscosity of the medium.

An embodiment provides that the sensor unit is a mechanically oscillatable unit with a driving/receiving unit, which excites the oscillatable unit to execute oscillations and receives the oscillations and converts them into an electrical, received signal, and that the electronics unit is embodied to control the oscillation excitement and to evaluate the received signal in reference to the process variable.

Another embodiment provides that the sensor unit is embodied as a conductive or capacitive probe having at least one electrode and that the electronics unit is embodied to supply the electrode with an electrical, transmitted signal, to receive an electrical, received signal and to evaluate the received signal in reference to the process variable.

BRIEF DESCRIPTION OF THE DRAWINGS

The invention will now be explained in greater detail based on the appended drawing, the figures of which show as follows.

DETAILED DISCUSSION IN CONJUNCTION WITH THE DRAWINGS

Figure 1:
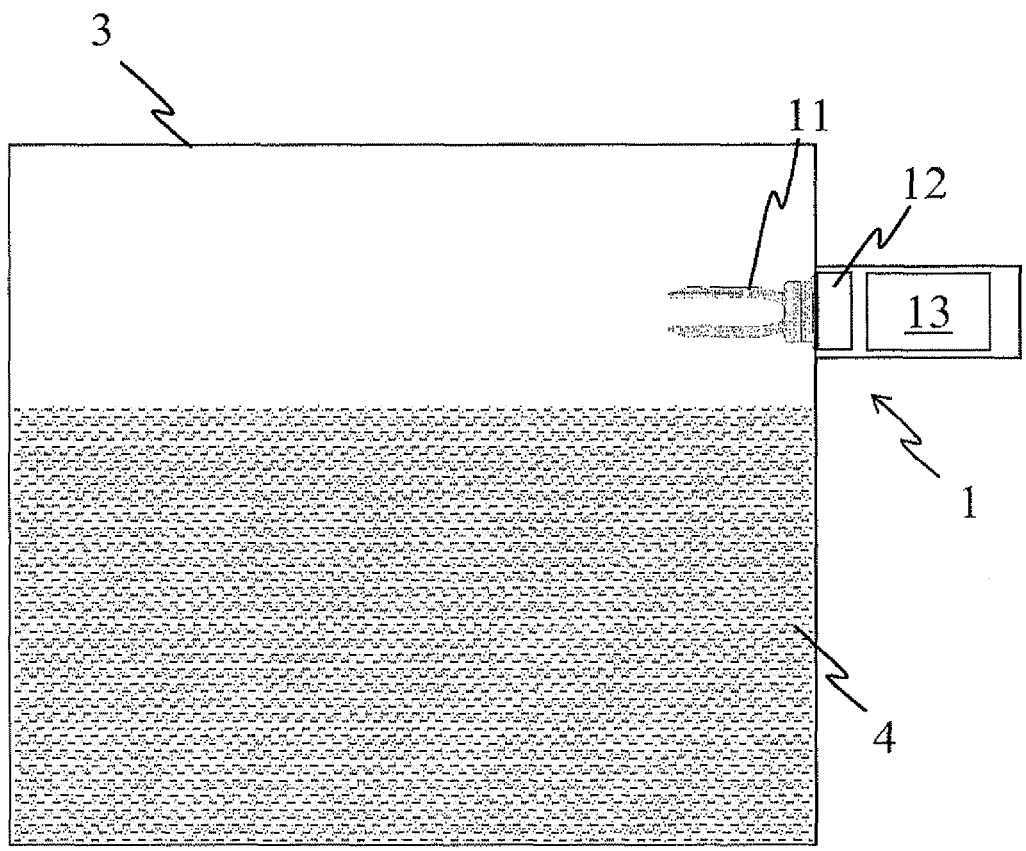
FIG. 1 is a schematically, a vibronic measuring device.

FIG. 1 shows a vibronic measuring device 1 for determining and/or monitoring a limit level, the density, or the viscosity of a medium in a container. Such an apparatus for monitoring a predetermined limit level is also referred to as a vibronic limit level switch. The measuring device 1 is positioned at a fill level height to be monitored in such a manner in the container 3 that the oscillatable unit 11 protrudes inwardly into the container 3, while the housing remains outside of the container 3. The oscillatable unit 11 is formed of two tines, which are coupled with one another via a membrane and are excitable via such membrane to execute mechanical oscillations. Arranged on the rear-side of the membrane facing away from the medium 4 is an electromechanical transducer unit 12, which excites the oscillatable unit 11 to execute resonant mechanical oscillations and receives mechanical oscillations from such and converts them into an electrical, received signal. The driving/receiving unit 12 is formed, for example, of one or more piezoelectric or inductive, transducer elements.

Instead of the two oscillatory tines, the oscillatable unit 11 can also be formed of one oscillatory rod or just a membrane.

The excitation to oscillations occurs, as a rule, via an analog oscillatory circuit, wherein a phase shift between exciter signal and received signal is fixedly predetermined, or digitally by means of a so-called frequency sweep, in the case of which the exciter signal continuously passes through a predetermined frequency band in discrete steps and, in such case, also passes through the resonant frequency.

For determining the process variable, the electronics unit 13 evaluates at least one oscillatory characteristic on the basis of the received signal. For this, the electronics unit 13 includes a logic unit, for example, in the form of a microcontroller or a FPGA (field programmable gate array). For fill level measurement, the logic unit evaluates the oscillation frequency in the case of exciting to resonant oscillations, in that it compares the measured frequency with a furnished, limit frequency. If the oscillation frequency lies below this threshold value, the oscillatable unit 11 is covered with medium 4; if it lies above, the oscillatable unit 11 is oscillating freely.

Analogously to the limit-level, there are also furnishable, for the density and for the viscosity, threshold values, whose exceeding or subceeding is detectable and issuable in the form a switch signal.

Limit level switches are frequently applied as overfilling preventers or as running empty protection in the case of pumps. The output signal of the limit level switch, for example, a 4-20 mA signal, is fed, for this, to a process controller, which, as a function of the output signal, controls actuators, such as, for example, valves or pumps, arranged downstream.

Besides vibronic limit level switches, also known are limit level switches working on the conductive or capacitive principle. These have a probe unit with at least one electrode, which is supplied with an electrical, exciter signal. From the capacitance between the electrode and a ground electrode or the container wall or based on the conductivity, the fill level is determinable.

The invention will be explained here using the example of an oscillatory fork as limit level switch. The invention is, however, equally applicable in the case of other apparatuses for registering limit values of process variables and for outputting switch signals, especially in the case of limit level switches. In other words, the measuring device can be any arbitrary measuring device for outputting two states.

Figure 2:
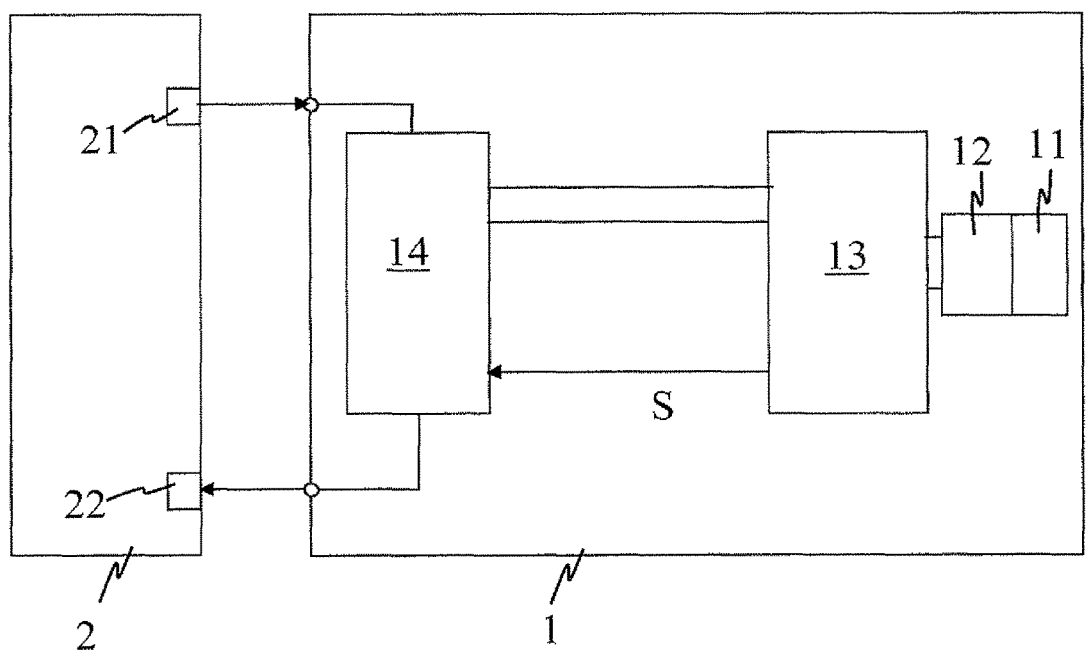
FIG. 2 is a schematically, the components of a vibronic measuring device and its energy supply.

FIG. 2 shows a block diagram of a vibronic limit level switch of the invention. This produces an output signal in the form a switch signal, which can assume two values, wherein one value means "covered" and the other value means "free".

In contrast to limit level switches known from the state of the art, the limit level switch of the invention does not require two conductors for energy supply and a third for transmission of the output signal to a downstream recorder apparatus for recording and/or graphical representation of the measured values of the limit level switch or to a process control system. Rather, two conductors are sufficient. In line with this, the measuring device 1 is connected with two conductors, one to a voltage output 21 and one to a digital input 22 of the process control system 2, for example, a PLC. The voltage output 21 provides a constant voltage—for example, 24 V. The power required for operation of the measuring device 1 lies, as a rule, in the order of magnitude of 1-10 mW and, thus, can be withdrawn from the process control system 2 without problem.

The voltage control system 14 of the measuring device 1 is connected between the two terminals and connects the voltage output 21 with the digital input 22. Dependent on the switch state representing, measurement signal S, which is fed to the voltage control system 14 from the electronics unit 13, the voltage control system 14 sets the terminal voltage at a first or second value. In order to produce an unequivocal output signal, the first value lies, for example, between 1 and 5 V and the second value between 20 and 24 V, preferably at 5 V and 20 V, respectively. The setting of the terminal voltage occurs, for example, via a controlling of the internal resistance of the voltage control system 14. Preferably, the two resistance values are selected in such a manner that the power withdrawal is equal for the two values of the terminal voltage. The electronics unit 13 is, thus, provided with a constant power, independently of the switch state.

The invention claimed is:

1. An apparatus for determining and/or monitoring at least one limit value of a process variable of a medium in a container, comprising:
   at least one sensor unit for registering a measured value dependent on the process variable;
   a voltage control system, which connects a voltage output with a digital input; and
   at least one electronics unit for producing a measurement signal dependent on the process variable, wherein:
   the apparatus is embodied to draw energy via a voltage output and a digital input of a recorder apparatus or a process control system; and
   said voltage control system controls a terminal voltage of the apparatus as a function of the measurement signal.

2. The apparatus as claimed in claim 1, the measurement signal is a switch signal, which assumes one of two possible states as a function of the process variable.

3. The apparatus as claimed in claim 1, wherein:
   said voltage control system supplies said electronics unit with a constant power.

4. The apparatus as claimed in claim 1, wherein:
   said voltage control system has a changeable internal resistance.

5. The apparatus as claimed in claim 1, wherein:
   at least one of the recorder apparatus and process control system is a programmable logic controller or a digital screen recorder.

6. The apparatus as claimed in claim 1, wherein:
   the process variable is a limit-level of a liquid or a bulk good in the container or a limit value for the density or the viscosity of the medium.

7. The apparatus as claimed in claim 1, wherein:
   said sensor unit is a mechanically oscillatable unit with a driving/receiving unit, which excites said oscillatable unit to execute oscillations and receives the oscillations and converts them into an electrical, received signal; and
   said electronics unit is embodied to control the oscillation excitement and to evaluate the received signal in reference to the process variable.

8. The apparatus as claimed in claim 1, wherein:
   said sensor unit is embodied as a conductive or capacitive probe having at least one electrode; and said electronics unit is embodied to supply the electrode with an electrical, transmitted signal, to receive an electrical, received signal and to evaluate the received signal in reference to the process variable.

\* \* \* \* \*